United States Patent
Yeo et al.

(10) Patent No.: US 11,154,514 B2
(45) Date of Patent: Oct. 26, 2021

(54) QUINIC ACID-MODIFIED NANOPARTICLES AND USES THEREOF

(71) Applicant: Purdue Research Foundation, West Lafayette, IN (US)

(72) Inventors: Yoon Yeo, West Lafayette, IN (US); Jun Xu, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 27 days.

(21) Appl. No.: 16/612,038

(22) PCT Filed: May 8, 2018

(86) PCT No.: PCT/US2018/031464
§ 371 (c)(1),
(2) Date: Nov. 8, 2019

(87) PCT Pub. No.: WO2018/208700
PCT Pub. Date: Nov. 15, 2018

(65) Prior Publication Data
US 2020/0060989 A1 Feb. 27, 2020

Related U.S. Application Data

(60) Provisional application No. 62/502,847, filed on May 8, 2017.

(51) Int. Cl.
*A61K 31/05* (2006.01)
*A61P 35/00* (2006.01)
*A61K 9/16* (2006.01)

(52) U.S. Cl.
CPC .............. *A61K 31/05* (2013.01); *A61K 9/167* (2013.01); *A61K 9/1647* (2013.01); *A61P 35/00* (2018.01)

(58) Field of Classification Search
CPC ...... A61K 31/05; A61K 9/1647; A61K 9/167; A61P 35/00
See application file for complete search history.

(56) References Cited

U.S. PATENT DOCUMENTS

2016/0338959 A1 11/2016 Troiano et al.

OTHER PUBLICATIONS

International Searching Authority, International Search Report, PCT Application Serial No. PCT/US2018/031464, dated Jul. 9, 2018.
International Searching Authority, Written Opinion of the International Searching Authority, PCT Application Serial No. PCT/US2018/031464, dated Jul. 9, 2018.
Amoozgar, Z et al., Development of Quinic Acid-Conjugated Nanoparticles as a Drug Carrier to Solid Tumors, Biomacromolecules, Jul. 8, 2013; 14(7): 2389-2395, Am Chem Society, USA.
Park, J et al., Polydopamine-Based Simple and Versatile Modification of Polymeric Nano Drug Carriers, ACS Nano, Apr. 22, 2014; 8(4): 3347-3356, Am Chem Society, USA.
European Patent Office, Supplementary European Search Report, EP Application No. 18798352.3, dated Apr. 17, 2020, EU.
European Patent Office, Examination Report Pursuant to Article 94(3) EPC, EP Application No. 18798352.3, dated Mar. 17, 2021, EU.
Intellectual Property Indian Patent Office, Examination Report, Indian Patent Application No. 201927045780, dated Apr. 5, 2021, IN.
Kaila et al., Quinic Acid Derivatives as Sialyl LewisX-Mimicking Selection Inhibitors: Design, Synthesis, and Crystal Structure in Complex with E-Selectin, J. Med. Chem. 2005, 48: 4346-4357, ACS Publications, US.

*Primary Examiner* — Robert S Cabral
(74) *Attorney, Agent, or Firm* — Reichel Stohry Dean LLP; Natalie J. Dean; Mark C. Reichel

(57) ABSTRACT

The present invention generally relates to targeted nanoparticle delivery to E-selectin- or P-selectin-positive cells or tissues. In particular, this invention discloses a method for preparing quinic acid-modified nanoparticles for targeted drug delivery to cancerous cells or tissues via E-selectin- or P-selectin-mediated transcytosis. The invention described herein also pertains to pharmaceutical compositions and methods for treating cancers.

19 Claims, 10 Drawing Sheets

QUINIC ACID-MODIFIED NANOPARTICLES AND USES THEREOF

CROSS-REFERENCE TO RELATED APPLICATIONS

The present U.S. patent application relates to, claims the priority benefit of, and is a 35 U.S.C. 371 national stage application of International Patent Application Serial No. PCT/US2018/031464 to Yeo et al., filed May 8, 2018, which relates to and claims the priority benefit of U.S. Provisional Patent Application Ser. No. 62/502,847, filed May 8, 2017. The entire contents of each of the aforementioned priority applications are hereby expressly incorporated by reference in their entireties into this disclosure.

GOVERNMENT SUPPORT CLAUSE

This invention was made with government support under a grant EB017791, awarded by the National Institute of Health. The government has certain rights in the invention.

TECHNICAL FIELD

The present invention generally relates to targeted nanoparticle delivery to E-selectin-positive cells or tissues. In particular, this invention discloses a method for preparing quinic acid-modified nanoparticles for targeted drug delivery to cancerous cells or tissues via E-selectin-mediated transcytosis. The invention described herein also pertains to pharmaceutical compositions and methods for treating cancers.

BACKGROUND

This section introduces aspects that may help facilitate a better understanding of the disclosure. Accordingly, these statements are to be read in this light and are not to be understood as admissions about what is or is not prior art.

Cancer is a group of most diverse diseases involving abnormal cell growth. Currently there are more than 100 types of identified cancer that affect human beings as well as animals. In 2016, there were an estimated 1,685,210 new human cancer cases diagnosed and 595,690 cancer deaths in the U.S. alone (Cancer Statistics 2016—American Cancer Society, Inc.). There are unmet and increasing needs for new and novel therapies to fight cancers.

Nanoparticles (NPs) have been considered a promising carrier of chemotherapeutic drugs. The premise of NP-based chemotherapy is predicated on the notion that tumors tend to develop hypervasculature and poor lymphatic systems, which provide selective access for NPs relative to normal tissues (Y Matsumura, *Cancer Res.* 1986, 46, 6387-6392). This phenomenon, called the enhanced permeability and retention (EPR) effect, has become the governing principle of NP-based drug delivery, irrespective of tumor-targeting mechanisms. Nevertheless, the promise of the NP-based chemotherapy has recently been challenged, due to the low percentage of NP accumulation in tumors (S Wilhelm, et al., *Nature Review Materials* 2016, 1, 1-12) and the lack of clinical evidence supporting the benefits of NPs. One of the potential reasons that limit NP delivery to tumors may be the diverse nature of the disease and high inter- and intra-subject difference, which result in variable efficiency of the EPR effect (E Karathanasis, et al., *PLoS One* 2009, 4, e5843). For the clinical success of NP-based chemotherapy for cancer treatment, additional means are needed to leverage the EPR effect and enhance the delivery efficiency of NPs beyond the level currently possible.

SUMMARY OF THE INVENTION

In some embodiments, the present invention is related to a quinic acid-modified nanoparticle (QANP) selectively targeting E-selectin- or P-selectin-positive cells or tissues comprising:
a. a nanoparticle (NP);
b. a polyphenol compound; and
c. a quinic acid derivative, wherein said NP is coated with said polyphenol compound, which is further modified by said quinic acid derivative.

In some embodiments, the present invention is related to a quinic acid-modified nanoparticle (QANP) selectively targeting E-selectin- or P-selectin-positive cells or tissues disclosed herein, wherein said NP is selected from the group consisting of poly(lactic-co-glycolic acid) (PLGA), polyethyleneglycol-PLGA conjugate, D-α-Tocopherol polyethylene glycol 1000 succinate (TPGS)-PLGA conjugate, polylactic acid (PLA), mesoporous silica, liposomes, and polyphenol aggregates.

In some embodiments, the present invention is related to a quinic acid-modified nanoparticle (QANP) selectively targeting E-selectin- or P-selectin-positive cells or tissues disclosed herein, wherein said NP comprises one or more encapsulated therapeutic drugs.

In some embodiments, the present invention is related to a quinic acid-modified nanoparticle (QANP) selectively targeting E-selectin- or P-selectin-positive cells or tissues disclosed herein, wherein said therapeutic drug is selected from the group consisting of paclitaxel, sorafenib, itraconazole, docetaxel, doxorubicin, bortezomib, carfilzomib, camptothecin, cisplatin, oxaliplatin, cytarabine, vincristine, irinotecan, amphotericin B, gemcitabine, polymyxin B, dexamethasone, and vitamin D.

In some embodiments, the present invention is related to a quinic acid-modified nanoparticle (QANP) selectively targeting E-selectin- or P-selectin-positive cells or tissues disclosed herein, wherein said polyphenol compound is polymerized dopamine (pD).

In some other embodiments, the present invention is related to a quinic acid-modified nanoparticle (QANP) selectively targeting E-selectin- or P-selectin-positive cells or tissues disclosed herein, wherein said quinic acid derivative is

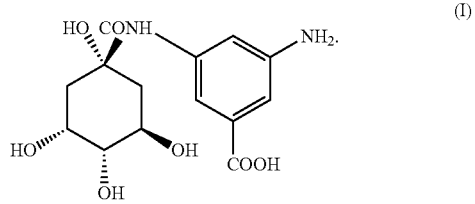

In some embodiments, the present invention is related to a quinic acid-modified nanoparticle (QANP) selectively targeting E-selectin- or P-selectin-positive cells or tissues disclosed herein, wherein said P-selectin or E-selectin-positive cells or tissues are cancerous cells or tissues, or endothelial cells surrounding cancerous cells or tissues.

In some other embodiments, the present invention is related to a pharmaceutical composition comprising a QANP disclosed herein, together with one or more diluents, excipients or carriers.

In some embodiments, the present invention is related to a pharmaceutical composition comprising a QANP disclosed herein, together with one or more diluents, excipients or carriers, wherein said pharmaceutical composition is for treating a patient with cancer.

In some embodiments, the present invention is related to a process for manufacturing a quinic acid-modified nanoparticle (QANP) selectively targeting E-selectin- or P-selectin-positive cells or tissues comprising the steps of:
a. preparing a nanoparticle (NP);
b. coating said NP with a polyphenol compound; and
c. modifying polyphenol coated NP with a quinic acid derivative to afford said QANP.

In some embodiments, the present invention is related to a process for manufacturing a quinic acid-modified nanoparticle (QANP) selectively targeting E-selectin- or P-selectin-positive cells or tissues disclosed herein, wherein said NP comprises one or more therapeutic drugs.

In some embodiments, the present invention is related to a process for manufacturing a quinic acid-modified nanoparticle (QANP) selectively targeting E-selectin- or P-selectin-positive cells or tissues disclosed herein, wherein said polyphenol compound is polymerized dopamine (pD).

In some embodiments, the present invention is related to a process for manufacturing a quinic acid-modified nanoparticle (QANP) selectively targeting E-selectin- or P-selectin-positive cells or tissues disclosed herein, wherein said quinic acid derivative is

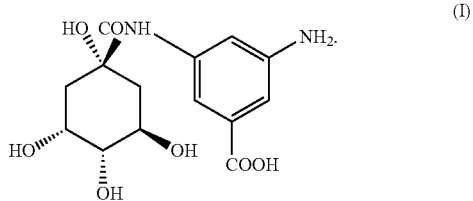

(I)

In some embodiments, the present invention is related to a process for manufacturing a quinic acid-modified nanoparticle (QANP) selectively targeting E-selectin- or P-selectin-positive cells or tissues disclosed herein, wherein said NP is made of PLGA, polyethyleneglycol-PLGA conjugate, D-α-Tocopherol polyethylene glycol 1000 succinate (TPGS)-PLGA conjugate, polylactic acid (PLA), mesoporous silica, liposomes, and polyphenol aggregates.

In some embodiments, the present invention is related to a pharmaceutical product manufactured according to the process of disclosed herein, together with one or more diluents, excipients or carriers.

In some embodiments, the present invention is related to a pharmaceutical composition manufactured according to the process of disclosed herein, together with one or more diluents, excipients or carriers.

In some embodiments, the present invention is related to a method for treating a patient of cancer comprising the step of administering to a patient in need of relief from said cancer a therapeutically effective amount of a pharmaceutical composition disclosed herein.

In some embodiments, the present invention is related to use of a pharmaceutical composition disclosed herein in the manufacture of a medicament for treating cancer in a subject.

In some other embodiments, the present invention is related to a pharmaceutical composition comprising nanoparticles of one or more compounds disclosed herein, together with one or more diluents, excipients or carriers.

DETAILED DESCRIPTION

Figure 1:
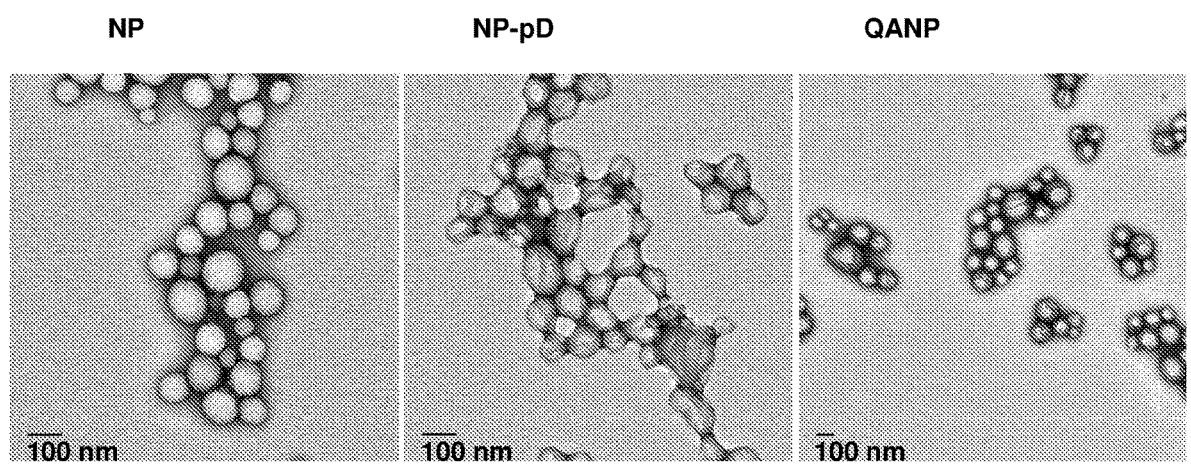
FIG. 1 shows transmission electron micrographs of PLGA NPs (left); PLGA-pD NPs (middle); QANPs (right). Negative staining with uranyl acetate. Scale bar: 100 nm.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

In some embodiments, the present invention is related to a quinic acid-modified nanoparticle (QANP) selectively targeting E-selectin- or P-selectin-positive cells or tissues comprising:
a. a nanoparticle (NP);
b. a polyphenol compound; and
c. a quinic acid derivative, wherein said NP is coated with said polyphenol compound, which is further modified by said quinic acid derivative.

In some embodiments, the present invention is related to a quinic acid-modified nanoparticle (QANP) selectively targeting E-selectin- or P-selectin-positive cells or tissues disclosed herein, wherein said NP is selected from the group consisting of poly(lactic-co-glycolic acid) (PLGA), polyethyleneglycol-PLGA conjugate, D-α-Tocopherol polyethylene glycol 1000 succinate (TPGS)-PLGA conjugate, polylactic acid (PLA), mesoporous silica, liposomes, and polyphenol aggregates.

In some embodiments, the present invention is related to a quinic acid-modified nanoparticle (QANP) selectively targeting E-selectin- or P-selectin-positive cells or tissues disclosed herein, wherein said NP comprises one or more encapsulated therapeutic drugs.

In some embodiments, the present invention is related to a quinic acid-modified nanoparticle (QANP) selectively targeting E-selectin- or P-selectin-positive cells or tissues disclosed herein, wherein said therapeutic drug is selected from the group consisting of paclitaxel, sorafenib, itraconazole, docetaxel, doxorubicin, bortezomib, carfilzomib, camptothecin, cisplatin, oxaliplatin, cytarabine, vincristine, irinotecan, amphotericin B, gemcitabine, polymyxin B, dexamethasone, and vitamin D.

In some embodiments, the present invention is related to a quinic acid-modified nanoparticle (QANP) selectively targeting E-selectin- or P-selectin-positive cells or tissues disclosed herein, wherein said polyphenol compound is polymerized dopamine (pD).

In some other embodiments, the present invention is related to a quinic acid-modified nanoparticle (QANP) selectively targeting E-selectin- or P-selectin-positive cells or tissues disclosed herein, wherein said quinic acid derivative is

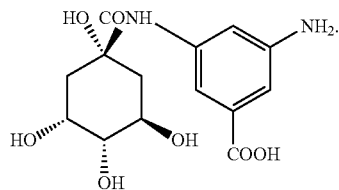

In some embodiments, the present invention is related to a quinic acid-modified nanoparticle (QANP) selectively targeting E-selectin- or P-selectin-positive cells or tissues disclosed herein, wherein said P-selectin or E-selectin-positive cells or tissues are cancerous cells or tissues, or endothelial cells surrounding cancerous cells or tissues.

In some other embodiments, the present invention is related to a pharmaceutical composition comprising a QANP disclosed herein, together with one or more diluents, excipients or carriers.

In some embodiments, the present invention is related to a pharmaceutical composition comprising a QANP disclosed herein, together with one or more diluents, excipients or carriers, wherein said pharmaceutical composition is for treating a patient with cancer.

In some embodiments, the present invention is related to a process for manufacturing a quinic acid-modified nanoparticle (QANP) selectively targeting E-selectin- or P-selectin-positive cells or tissues comprising the steps of:
a. preparing a nanoparticle (NP);
b. coating said NP with a polyphenol compound; and
c. modifying polyphenol coated NP with a quinic acid derivative to afford said QANP.

In some embodiments, the present invention is related to a process for manufacturing a quinic acid-modified nanoparticle (QANP) selectively targeting E-selectin- or P-selectin-positive cells or tissues disclosed herein, wherein said NP comprises one or more therapeutic drugs.

In some embodiments, the present invention is related to a process for manufacturing a quinic acid-modified nanoparticle (QANP) selectively targeting E-selectin- or P-selectin-positive cells or tissues disclosed herein, wherein said polyphenol compound is polymerized dopamine (pD).

In some embodiments, the present invention is related to a process for manufacturing a quinic acid-modified nanoparticle (QANP) selectively targeting E-selectin- or P-selectin-positive cells or tissues disclosed herein, wherein said quinic acid derivative is

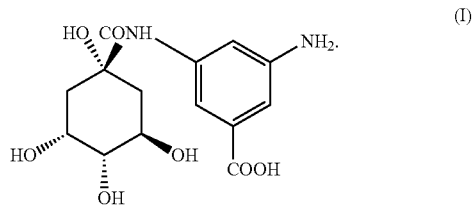

In some embodiments, the present invention is related to a process for manufacturing a quinic acid-modified nanoparticle (QANP) selectively targeting E-selectin- or P-selectin-positive cells or tissues disclosed herein, wherein said NP is made of PLGA, polyethyleneglycol-PLGA conjugate, D-α-Tocopherol polyethylene glycol 1000 succinate (TPGS)-

PLGA conjugate, polylactic acid (PLA), mesoporous silica, liposomes, and polyphenol aggregates.

In some embodiments, the present invention is related to a pharmaceutical product manufactured according to the process of disclosed herein, together with one or more diluents, excipients or carriers.

In some embodiments, the present invention is related to a pharmaceutical composition manufactured according to the process of disclosed herein, together with one or more diluents, excipients or carriers.

In some embodiments, the present invention is related to a method for treating a patient of cancer comprising the step of administering to a patient in need of relief from said cancer a therapeutically effective amount of a pharmaceutical composition disclosed herein.

In some embodiments, the present invention is related to use of a pharmaceutical composition disclosed herein in the manufacture of a medicament for treating cancer in a subject.

In some other embodiments, the present invention is related to a pharmaceutical composition comprising nanoparticles of one or more compounds disclosed herein, together with one or more diluents, excipients or carriers.

These and other features, aspects and advantages of the present invention will become better understood with reference to the following figures, descriptions and claims.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

Nanoparticles (NPs) have been considered a promising carrier of chemotherapeutic drugs. The premise of NP-based chemotherapy is predicated on the notion that tumors tend to develop hypervasculature and poor lymphatic systems, which provide selective access for NPs relative to normal tissues. This phenomenon, called the enhanced permeability and retention (EPR) effect, has become the governing principle of NP-based drug delivery, irrespective of tumor-targeting mechanisms. Nevertheless, the promise of the NP-based chemotherapy has recently been challenged, due to the low percentage of NP accumulation in tumors and the lack of clinical evidence supporting the benefits of NPs. One of the potential reasons that limit NP delivery to tumors may be the diverse nature of the disease and high inter- and intra-subject difference, which result in variable efficiency of the EPR effect. For the clinical success of NP-based chemotherapy, there should be additional means to leverage the EPR effect and enhance the delivery efficiency of NPs beyond the level currently possible.

In the absence of a reliable EPR effect, the vascular endothelium—the first cell layer encountered by circulating NPs—serves as an access barrier to the underlying tumors; therefore, NPs that can actively interact with the endothelial barrier will have a greater chance to extravasate into the tumors. In this regard, we note a distinctive array of adhesion molecules upregulated on the surface of the peritumoral endothelium (N Makrilia, et al., *Cancer Invest* 2009, 27, 1023-1037). For example, E-selectin, a transmembrane glycoprotein expressed on endothelial cells upon pro-inflammatory stimuli (GS Kansas, *Blood* 1996, 88, 3259-3287), is also overexpressed on the peritumoral endothelium, promoting angiogenesis (AE Koch, et al, *Nature* 1995, 376, 517) and tumor proliferation. Moreover, E-selectin serves as an adhesion point for circulating tumor cells and helps them to extravasate and form metastases (H Kobayashi, et al, *Current Medicinal Chemistry* 2007, 14, 377-386; GE Rice, et al, *Science* 1989, 246, 1303).

The natural ligand for E-selectin is a carbohydrate moiety, sialyl Lewis-x (sLe$^x$), a tetrasaccharide consisting of sialic acid, galactose, fucose, and N-acetyl-galactosamine (M Phillips, et al, *Science* 1990, 250, 1130-1132). Given the implication of E-selectin in tumor progression and metastasis, sLe$^x$ and its analogs have been explored as E-selectin antagonists (S Pedatella, et al, *Carohydrate Research* 2008, 343, 31-38). A number of chemical analogs of sLe$^x$ have been proposed to enhance its specificity and affinity for E-selectin (EE Simanek, et al, *Chemical Review* 1998, 98, 833-862). Among them, quinic acid (QA) along with its derivatives have been noted as promising candidates due to the stability, simplicity, and ease of chemical modification (N Kaila, et al, *J. Med. Chem.* 2005, 48, 4346-4357). These E-selectin ligands have also been used as targeting ligands of macromolecular and NP drug carriers for delivery of chemotherapeutic drugs to the peritumoral endothelium (Y Shamay, et al, *J. Controlled Release* 2015, 217, 102-112). Most recently, polymeric NPs coated with the membrane of inflammatory neutrophils were generated to address the premetastatic endothelium based on its interactions with adhesion molecules (T Kang, et al, *ACS Nano* 2017, 11, 1397-1411).

While these studies demonstrate the feasibility of using endothelium-targeting ligands for enhancing drug delivery to tumors, the complexity and inefficiency of new polymer synthesis can hamper clinical translation of this promising principle. To address this challenge, we employed a simple surface functionalization method based on dopamine polymerization, applicable to a variety of NP platforms irrespective of their chemical reactivity (J Park, et al., *ACS Nano* 2014, 8, 3347-3356). The dopamine polymerization method involves a simple incubation of NPs in dopamine solution in an oxidizing condition, which allows dopamine to polymerize and form a chemically reactive layer on the NP surface to accommodate ligand molecules (H Lee, et al, *Science* 2007, 318, 426-430). This method allows for conjugation of various types of ligands, including a QA derivative, and flexible control of the QA density on the NP surface. Such versatility and flexibility enable us to investigate the optimal condition for increasing transendothelial transport of NPs via QA and compare the QA-modified NPs with those containing typical stealth coating such as polyethylene glycol (PEG). In this study, we demonstrate polymeric NPs can be readily modified with QA via polymerized dopamine (polydopamine, pD) efficiently interact with activated endothelial cells to translocate the endothelial cell layer, and reach tumors to a much greater extent than typical stealth NPs do based on the EPR effect.

Synthesis of QA-NH$_2$, Synthetic Mimic of sLe$^x$

QA-NH$_2$, a synthetic mimic of sLe$^x$, was synthesized according to the previously reported scheme with slight modification. The overall yield was 62%. $^1$H proton NMR confirmed the structure of the compound. Electron spray ionization mass spectrometry found the mass to charge ratio of the compound to be 324.9 (−MS mode) as expected.

Fabrication and Characterization of QANPs

NP-pD-QA (QANPs) were prepared with the dopamine-mediated surface modification method (J Park, et al., *ACS Nano* 2014, 8, 3347-3356). PLGA NPs were first prepared by the single emulsion solvent evaporation method and covered with pD layer, which then accommodates QA-NH$_2$ on the NP surface via Michael addition and/or Schiff base reactions (H Lee, et al, *Science* 2007, 318, 426-430). QANPs had an average diameter of 145 nm and a zeta potential of −6.5 mV according to dynamic light scattering. The electron spray ionization mass spectrometry (MS-ESI) analysis of QANPs provided qualitative evidence for successful conjugation of QA-NH$_2$ on QANPs. PLGA NPs simply incubated with QA-NH$_2$ without pD functionalization (PLGA/QA NPs) had no QA-NH$_2$ signature peaks on MS-ESI, confirming the essential role of pD coating as a mediator of QA-NH$_2$ conjugation. Transmission electron micrographs (TEM) (FIG. 1) identified an additional layer on the surface of the PLGA core NPs due to pD coating (Table 1). However, there was no visible difference between PLGA-pD NPs and QANPs, consistent with previous examples using other ligands (J Park, et al, *ACS Nano* 2014, 8, 3347-3356).

The number of QA-NH$_2$ conjugated to the surface of QANPs was indirectly determined by subtracting the amount QA-NH$_2$ remaining in the reaction medium from the original QA-NH$_2$ feed. The QA-NH$_2$ conjugated to unit surface area of QANPs increased linearly with QA-NH$_2$ feed and did not reach a plateau with the range of tested feed.

TABLE 1

Particle size, zeta potential, and polydispersity index (PDI) of NPs.

| Name | Size (nm) | Zeta Potential (mV) | PDI |
|---|---|---|---|
| Bare NP | 134 ± 12 | −10.4 ± 9.3 | 0.1 ± 0.02 |
| NP-pD | 142 ± 17 | −11.2 ± 8.1 | 0.2 ± 0.06 |
| PEG-NP | 163 ± 11 | −10.7 ± 6.2 | 0.2 ± 0.04 |
| QA-NP | 151± 14 | −11.8 ± 4.9 | 0.1 ± 0.03 |
| QA-NP (PLGA-FITC) | 149 ± 7 | −9.3 ± 5.5 | 0.1 ± 0.03 |
| QA-NP (PLGA-Alexa 555) | 147 ± 11 | −10.4 ± 6.1 | 0.1 ± 0.05 |
| QA-NP (PLGA-ICG) | 154 ± 20 | −10.8 ± 5.7 | 0.1 ± 0.06 |
| Bare NP (PLGA-TPGS) | 171 ± 33 | −12.3 ± 6.6 | 0.2 ± 0.09 |
| PTX@PEG-NP (PLGA-TPGS) | 184 ± 41 | −11.5 ± 5.7 | 0.2 ± 0.07 |
| PTX@QA-NP (PLGA-TPGS) | 179 ± 26 | −10.8 ± 6.4 | 0.1 ± 0.04 |

Data: mean ± s.d. (n = 3 independent batches)

Stability of QANPs in Serum

Prior to biological evaluation of QANPs, their size distribution in 50% FBS was tested in various concentrations ranging from 0.05 mg/mL to 0.2 mg/mL. Irrespective of concentration, QANPs showed a consistent peak at 120 nm. The two distinctive peaks at 10 nm and 80 nm were identified to be serum proteins and their aggregates. Over 2 hours in 50% FBS, no aggregation or agglomeration of QANPs occurred.

Interaction of QANPs with Activated HUVECs

Figure 2A:
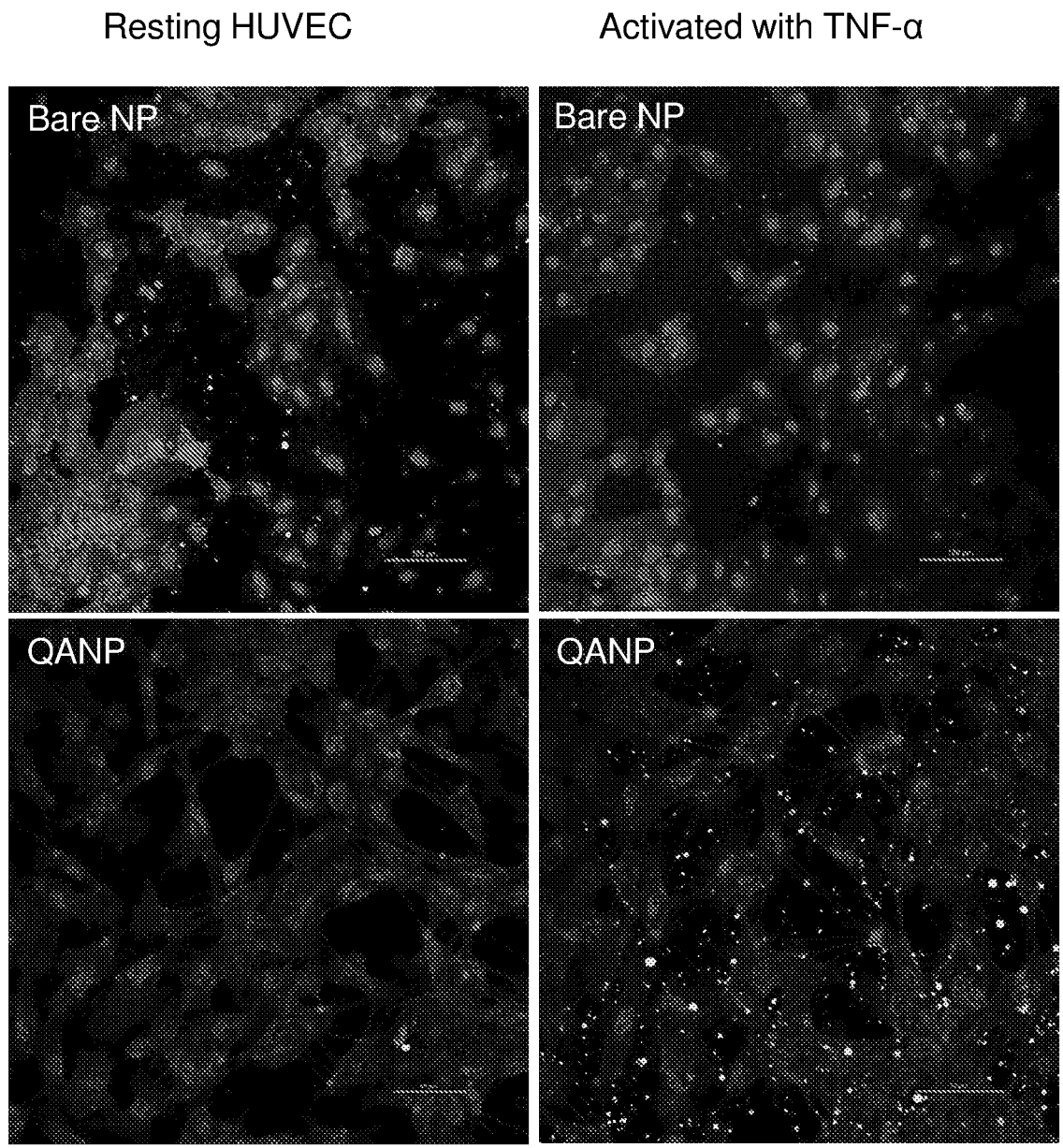
FIG. 2A depicts the confocal images of bare NPs and QANPs incubated with resting HUVEC and TNF-α-activated HUVEC. Green: NPs; blue: cell nuclei; red: plasma membrane.
Figure 2B:
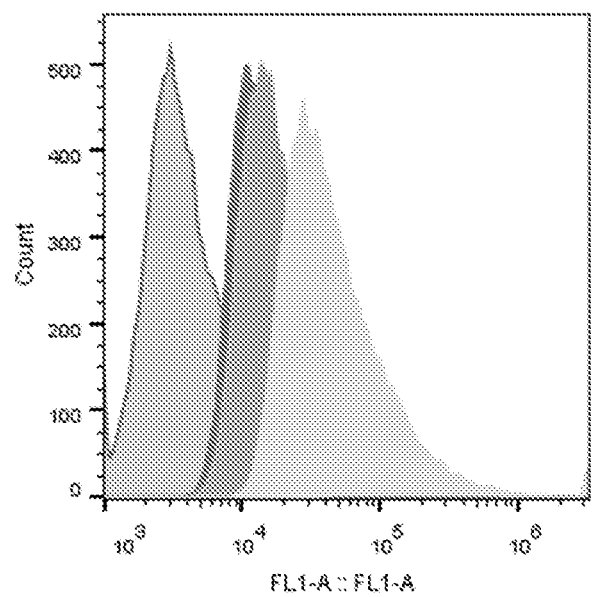
FIG. 2B represents a flow cytometry histogram of resting HUVEC and TNF-α-activated HUVEC.
Figure 2C:
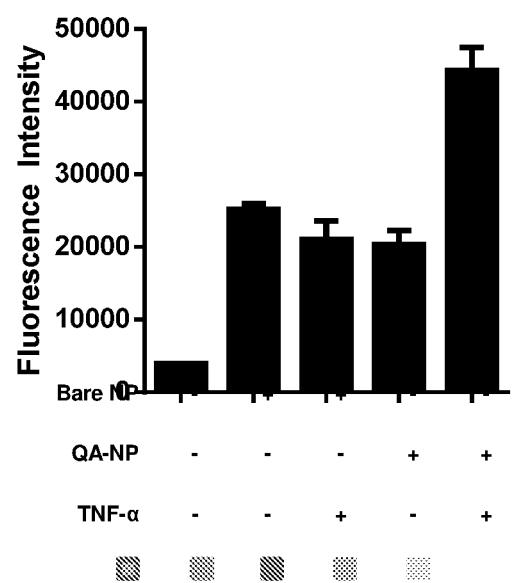
FIG. 2C shows the quantitative measurement of HUVEC cells interacting with bare NPs or QANPs.

QANP-HUVEC interaction was examined with confocal microscopy and flow cytometry (FIGS. 2A-2C). Specifically, HUVECs were incubated with fluorescently-labeled QANPs or bare NPs with or without TNF-α activation for 6 h. TNF-α treatment induces the expression of E-selectin on HUVECs. For comparison, bare PLGA NPs were also tested in the same manner. FIG. 2A shows that QANPs were associated with the HUVEC cell membrane whereas bare NPs showed minimal non-specific binding. To quantify the NPs retained with the cells, fluorescence intensity of the cell lysate was measured using flow cytometry. Activated HUVEC incubated with QANPs showed the greatest fluorescence intensity compared to control groups (non-activated HUVEC with QANPs (or bare NPs) or activated HUVEC with unmodified NPs), consistent with confocal imaging (FIGS. 2B, 2C). These results indicate that QANPs have the affinity for the activated HUVECs and thus have the potential to concentrate on the peritumoral endothelium.

Figure 3A:
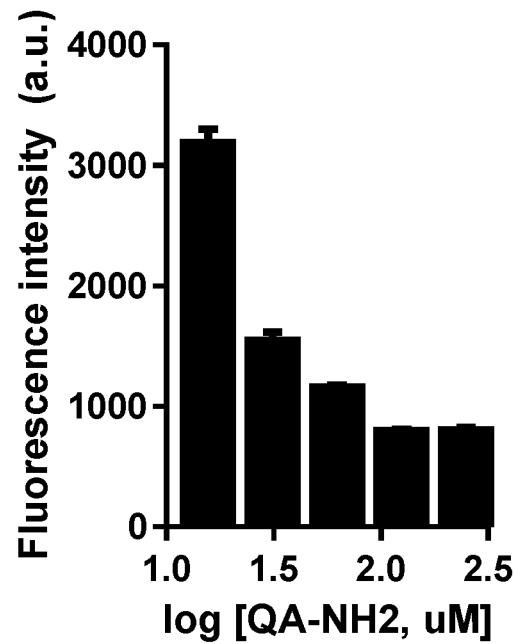
FIG. 3A Competitive inhibition of QANP binding to HUVECs by free QA-NH$_2$.
Figure 3B:
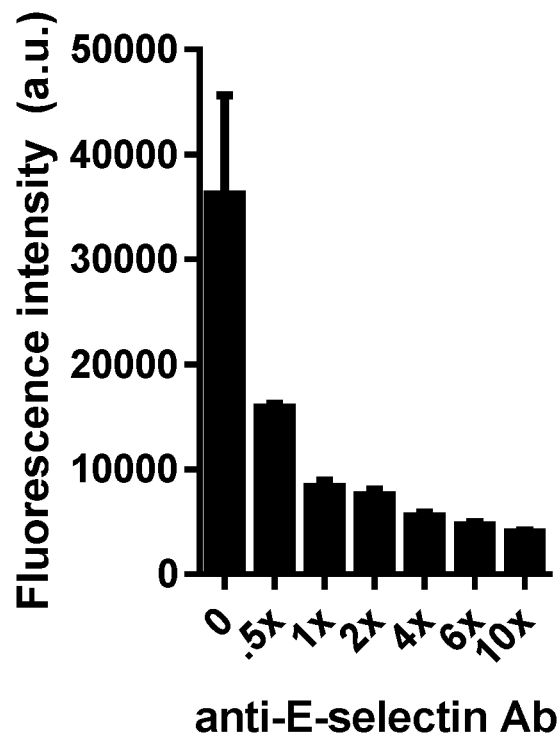
FIG. 3B demonstrates the competitive inhibition of QANP binding to HUVECs by an anti-E-selectin antibody. QANP-HUVEC binding was quantified by flow cytometry.

To confirm the mediators of QA-E-selectin interactions, the incubation was performed in the presence of free QA-NH$_2$ or anti-E-selectin antibodies. QANP binding to the activated HUVECs was reduced by free QA-NH$_2$ (FIG. 3A) and anti-E-selectin antibody (FIG. 3B) in a dose dependent manner, which indicates that free QA-NH$_2$ competes with QANPs and the blockade of E-selectin interferes with QANP binding to the activated HUVECs, respectively. These results confirm that the binding of QANPs to the activated HUVECs was mediated by the QA interaction with E-selectin.

Figure 4A:
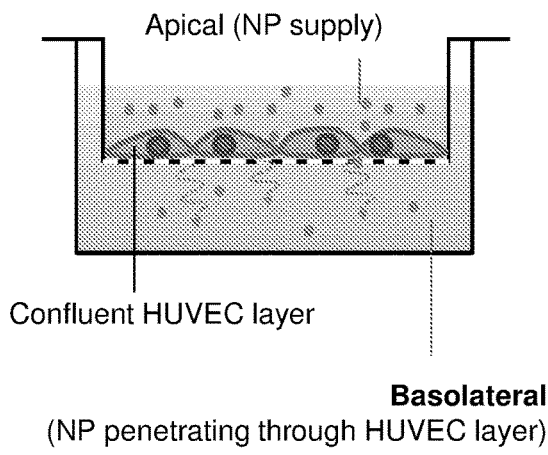
FIG. 4A is a schematic diagram of transendothelial migration assay.
Figure 4B:
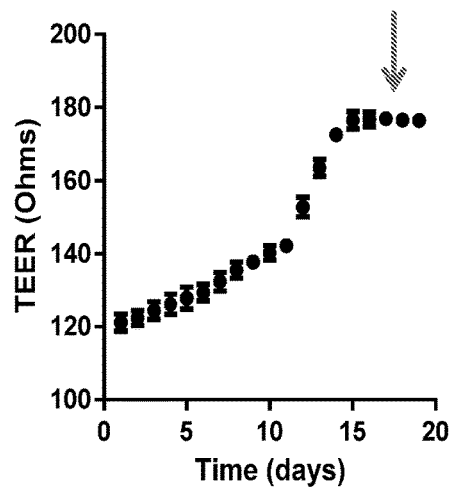
FIG. 4B is a representative TEER plot of HUVEC monolayer.
Figure 4C:
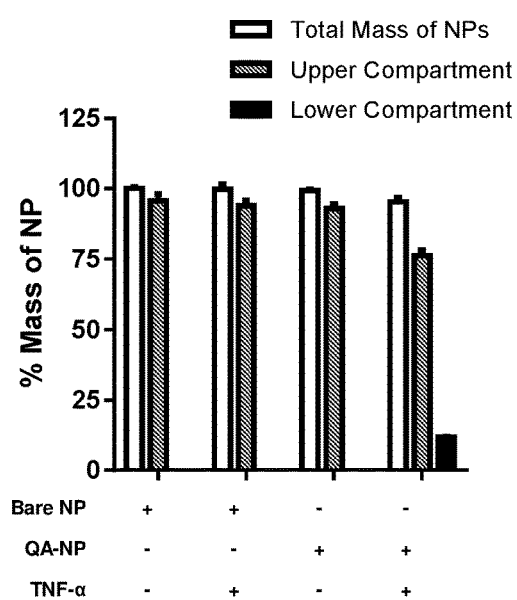
FIG. 4C shows the percentage of NP transport across confluent HUVEC monolayer with and without TNF-α activation.

Tranendothelial Migration Assay for Testing the Extravasation Potential of QANPs The interactions between QANPs and peritumoral endothelium help concentrate the NPs in the vicinity of the tumor and increase the chance for NPs to extravasate and reach tumors. We assessed the potential of QANPs to transport across endothelial cell layer grown on a Transwell insert (FIG. 4A), similar to the Boyden chamber assay (S Boyden, *J. Experimental Med.* 1962, March, 453-466). QANPs and control NPs were placed on the apical side of the Transwell containing confluent HUVEC layer (FIG. 4B), with and without TNF-α pre-treatment, and the NPs remaining in the apical side and recovered in the basolateral side were quantified. As expected, the transport across the endothelial layer was observed only with QANPs and TNF-α-activated (=E-selectin expressing) HUVEC (FIG. 4C).

Figure 4D:
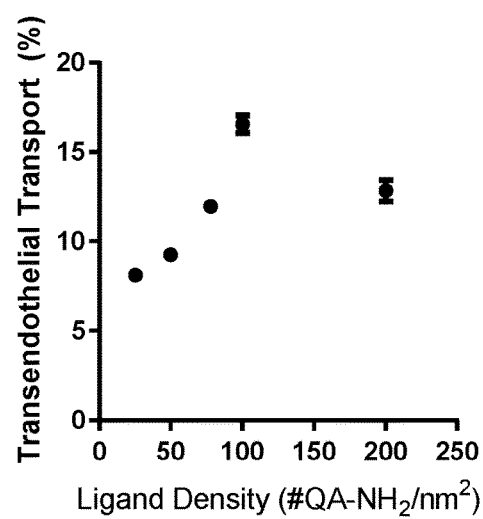
FIG. 4D shows the relationship between the ligand density and the transendothelial transport of QANPs.

To examine the relationship between ligand density and the transendothelial transport, QANPs at various ligand densities were incubated with the activated HUVECs (FIG. 4D). As the ligand density of QANPs increased from 25 QA-$NH_2$/$nm^2$ to 100 QA-$NH_2$/$nm^2$, QANP transport increased. However, when the ligand density further increased to 200 QA-$NH_2$/$nm^2$, the percentage of cells crossing the endothelial layer decreased. A potential explanation is that with the increase in the ligand density, QA-$NH_2$ may have formed intermolecular clustering due to hydrogen bonding, instead of interacting with E-selectin. Overall, the Transwell experiment suggests that QA ligands with an optimal surface density help transport NPs across the activated HUVEC.

Various Cancer Cells Induce E-Selectin Upregulation in Endothelial Cells

Figure 5A:
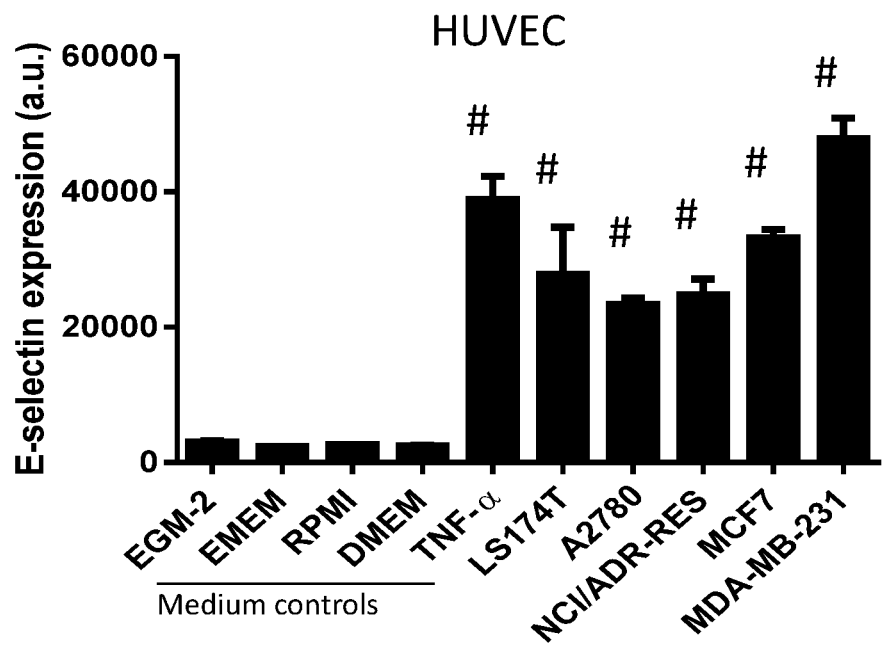
FIG. 5A shows the E-selectin expression of HUVEC grown in media conditioned with various human cancer cell lines. #: $p<0.001$ vs. EGM-2 group by Dunnett's multiple comparisons test following one-way ANOVA.
Figure 5B:
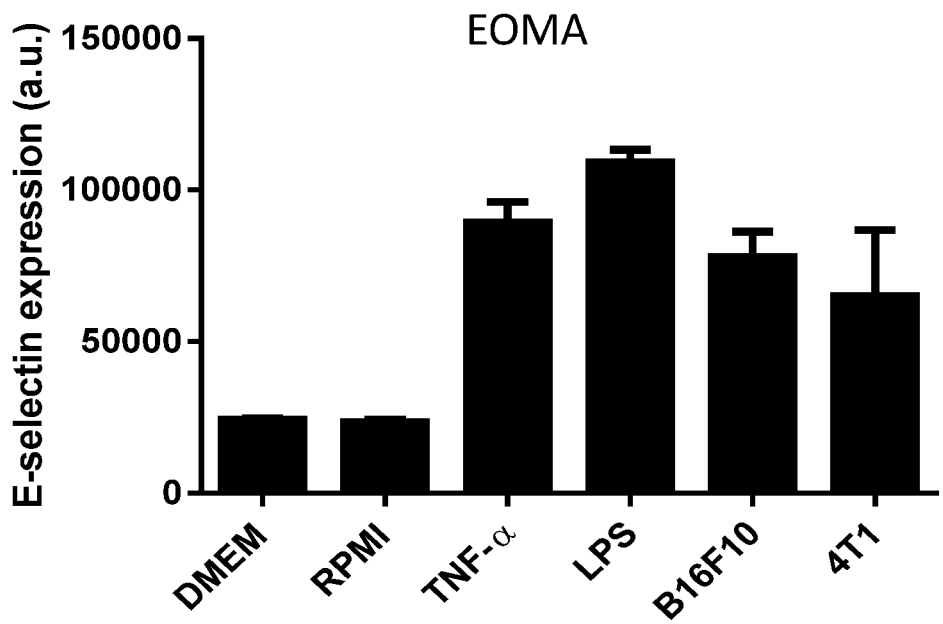
FIG. 5B shows the E-selectin expression of EOMA cells grown in media conditioned with various murine cancer cell lines. #: $p<0.001$; *: $p<0.01$ vs. DMEM group by Dunnett's multiple comparisons test following one-way ANOVA.

Vascular expression of E-selectin varies with the tumor type. Literature suggests strong correlation between E-selectin upregulation in endothelial cells and the amount of interleukin-1α secreted by tumors (M Nguyen, *Am J Pathol* 1997, 150, 1307-1314). We screened conditioned media of several human cancer cell lines to see if they induce E-selectin expression in HUVECs. HUVECs exposed to the conditioned media expressed different levels of E-selectin (FIG. 5A). MDA-MB-231-conditioned media induced the greatest level of E-selectin expression. A similar observation was obtained with a set of murine cell lines (FIG. 5B). Culture media conditioned with B16F10 melanoma cells or 4T1 breast cancer cells induced E-selectin expression, which indicates the broad applicability of E-selectin targeting.

To investigate whether the interaction between QA-NP and E/P-selectin helped QA-NP to extravasate and enter tumors, we used intravital microscopy to visualize QA-NP in mice with GFP-expressing MDA-MB-231 tumors. QA-NP was observed from 2 h post injection near the blood vessel. The QA-NP signal increased with time migrating further into the tumor. This observation coincides with in vitro Transwell result and provides in vivo proof-of-concept that QA-NP interaction with E/P-selectin improved extravasation and enhanced tumor accumulation.

In Vivo Whole Body Imaging of QANPs

Due to the positive effect of MDA-MB-231 on E-selectin expression on HUVECs, we chose a mouse model of MDA-MB-231 xenograft for evaluation of QANP distribution. We hypothesize that QANPs will develop active interactions with peritumoral endothelium via E-selectin, transcytose across the endothelium, and accumulate the NPs in MDA-MB-231 tumors to a greater extent than long-circulating NPs that depend on the EPR effect. To trace NP distribution over time with a whole body fluorescence imaging system, QANPs was labeled with indocyanine green (ICG), a near infrared fluorescence dye. ICG was covalently conjugated to PLGA via carbodiimide chemistry. Bare NPs made with ICG-PLGA conjugate (ICG-NPs) remained stable in NPs incubated in 50% FBS, in contrast to bare NPs physically encapsulating ICG (ICG/NP), indicating that the ICG fluorescence of the ICG-NPs will represent NPs in in-vivo imaging.

Figure 6:
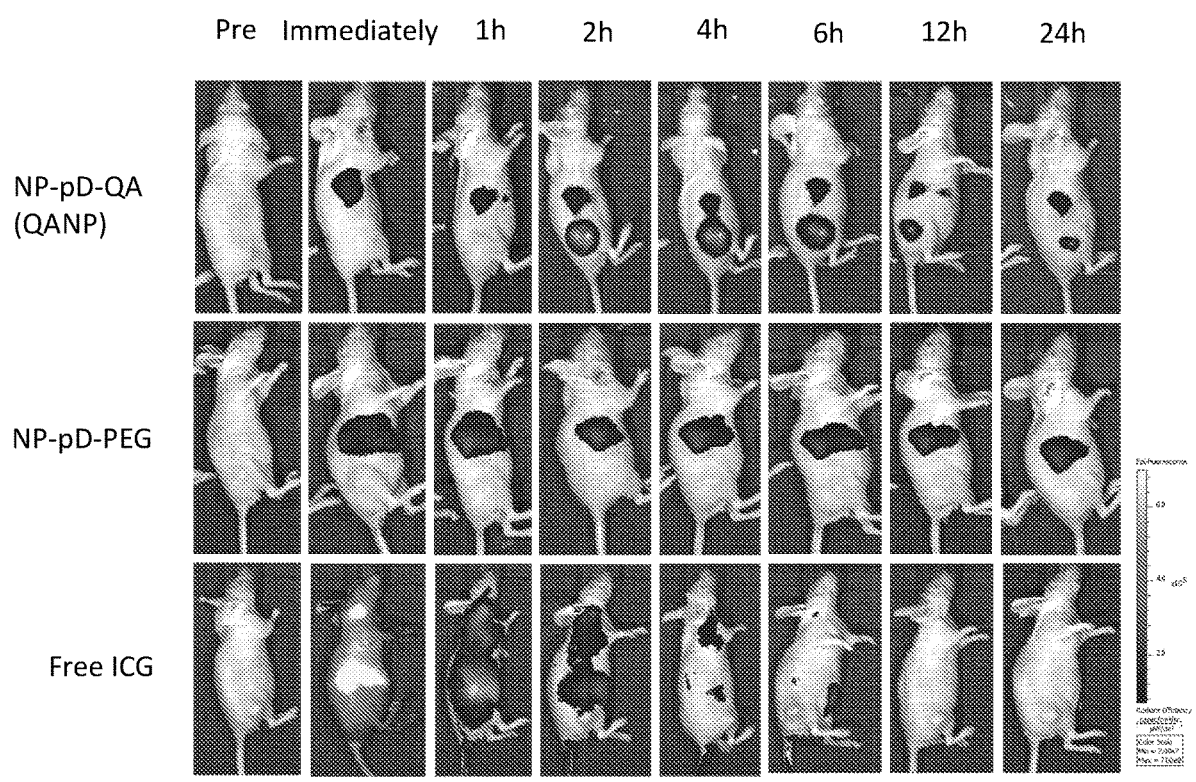
FIG. 6 shows representative whole body imaging of animals at 24 hour post-injection. Animals bearing subcutaneous MDA-MB-231 tumor xenografts were injected with QANPs (top), NP-pD-PEG (middle), and free ICG (bottom) via tail vein.

QANPs, NP-pD-PEG NPs (representing PEGylated, long-circulating NPs), and free ICG were injected via tail vein and imaged over 24 hours (FIG. 6). Free ICG spread throughout the body immediately following the administration and was gradually cleared by hepatobiliary elimination, whereas QANPs and NP-pD-PEG NPs showed up in the liver. Significant tumor accumulation of QANPs was observed starting at 2 hours post injection, whereas nearly no fluorescence was detected in animals treated with free ICG and NP-pD-PEG (Table 2). The QANPs accumulated in the tumor gradually decreased over time but lasted throughout the 24-hour experiment period. Animals receiving NP-pD-PEG and free ICG did not show fluorescence in tumors at all time points. It is curious that NP-pD-PEG was not observed at all in the tumor. Although not overly vascularized like LS174T xenografts, MDA-MB-231 xenograft is still more vascularized than muscle tissues, according to the extent of Evans blue accumulation (LS174T/muscle=1.34, MDA-MB-231/muscle=1.04). Literature also supports the vascularization of MDA-MB-231 tumors and accumulation of long-circulating NPs. We do not suspect that PEG modification in NP-pD-PEG was insufficient. It is more likely that the fluorescence detection threshold was set so high that weak fluorescence may not have been captured. This experiment was repeated with another set of animals to confirm the reproducibility of the result. Animals receiving QANPs and NP-pD-PEG showed differential fluorescence signals in tumors, consistent with the previous experiment.

TABLE 2

Plasma pharmacokinetic parameters of Taxol, PTX@PEG-NP, and PTX@QA-NP.

| Parameter | Unit | Taxol | PTX@PEG-NP | PTX@QA-NP |
|---|---|---|---|---|
| $AUC_{(0-t)}$ | ug/L*h | 7307 | 10075 | 11015 |
| $AUC_{(0-\infty)}$ | ug/L*h | 7383 | 10214 | 11623 |
| $MRT_{(0-t)}$ | h | 1.7 | 4.4 | 5.2 |
| $MRT_{(o-\infty)}$ | h | 2.0 | 5.2 | 6.5 |
| $T_{1/2}$ | h | 3.5 | 3.4 | 4.9 |
| $T_{max}$ | h | 2 | 0.5 | 0.5 |
| $V_{ss}$ | L/kg | 13.9 | 9.9 | 12.2 |
| CL | L/h/kg | 2.7 | 2.0 | 1.8 |
| $C_{max}$ | ug/L | 1760 | 3426 | 2411 |

Ex Vivo Analysis of QANPs' Organ Distribution

Figure 7A:
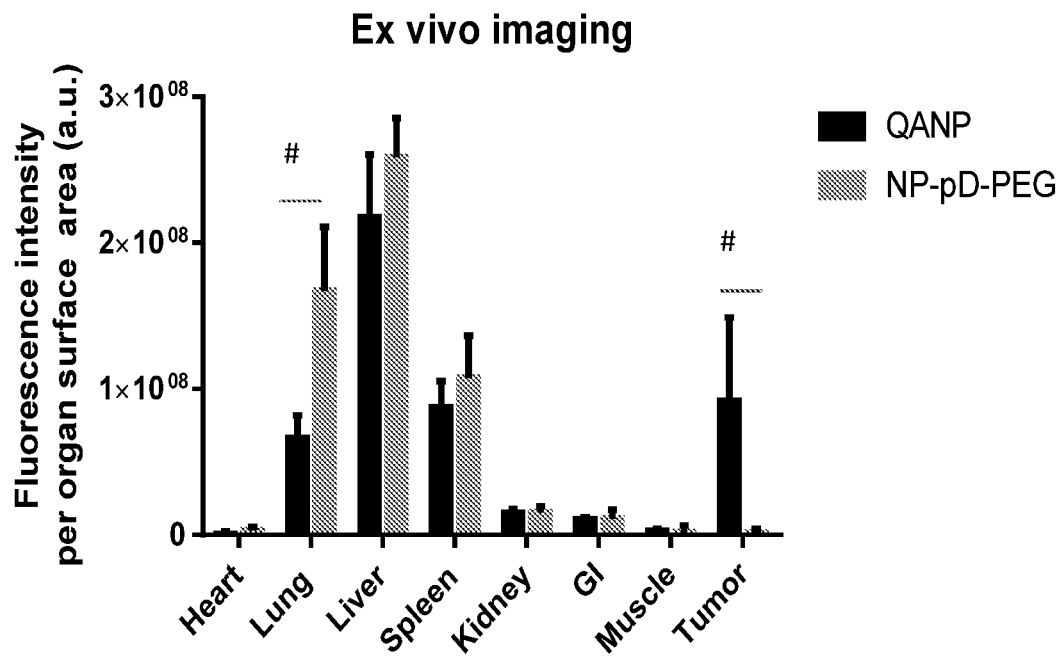
FIG. 7A depicts fluorescence intensity of ex vivo images of major organs retrieved at the end of whole body imaging. n=5 mice per group. #: $p<0.0001$ by Bonferroni's multiple comparisons test following two-way ANOVA.

Ex vivo analysis was performed immediately after the completion of whole body imaging. After the final imaging time point (24 h post injection), animals were sacrificed, and all major organs were retrieved for imaging. The finding was consistent with whole body imaging results (FIG. 7A). With animals receiving NP-pD-PEG, the liver showed the greatest fluorescence signal, followed by the lung and the spleen. While QANPs showed accumulation in the RES organs, they showed significantly higher signals in tumors and lower signals in the lungs than NP-pD-PEG. Ex vivo images at 6 h post-injection (obtained from the second set of experiment) showed that QANP signals in tumors were stronger than those in the liver or spleen and their signals in the liver and spleen were less intense than those of NP-pD-PEG.

Figure 7B:
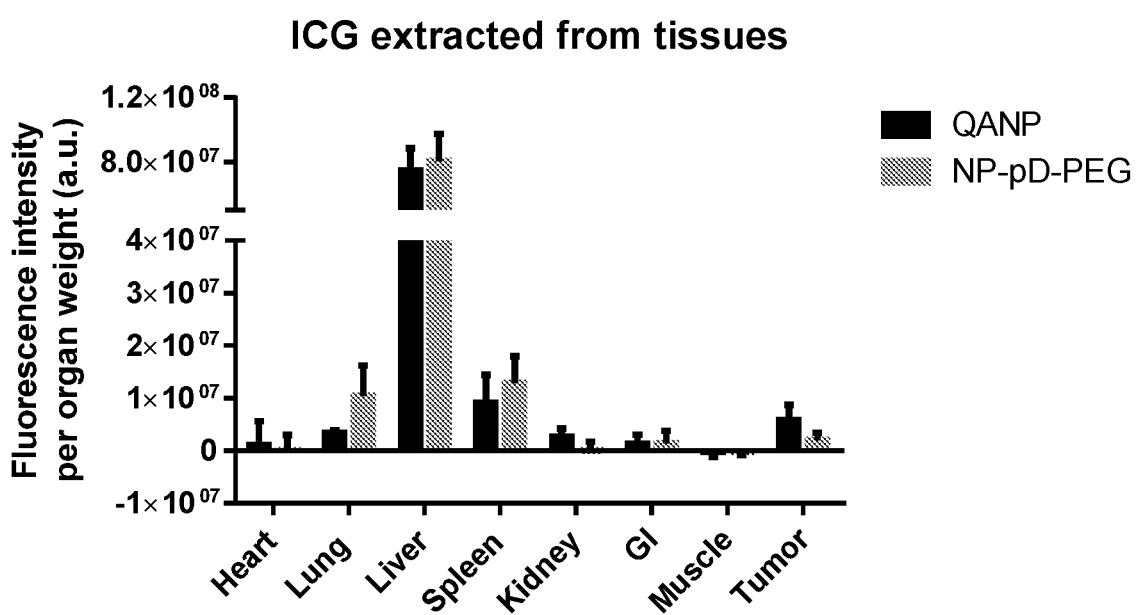
FIG. 7B shows fluorescence intensity of ICG extracted from the major organs. n=5 mice per group. #: $p<0.0001$ by Bonferroni's multiple comparisons test following two-way ANOVA.

ICG content in each organ was quantified by extracting the ICG-labeled polymer from tissue homogenates. Although the trend was consistent with that of ex-vivo imaging, the ICG level in the liver was substantially higher than those in other organs, and the difference between two NPs in each organ was not statistically significant (FIG. 7B). We attribute the discrepancy to the presence of additional dimension we took into consideration when using ICG extraction method (three-dimensional analysis for ICG extraction vs. two-dimensional surface analysis for ex vivo imaging) and/or incomplete extraction of ICG from dense tumors.

Anti-Cancer Efficacy: Comparison with Taxol

Figure 8A:
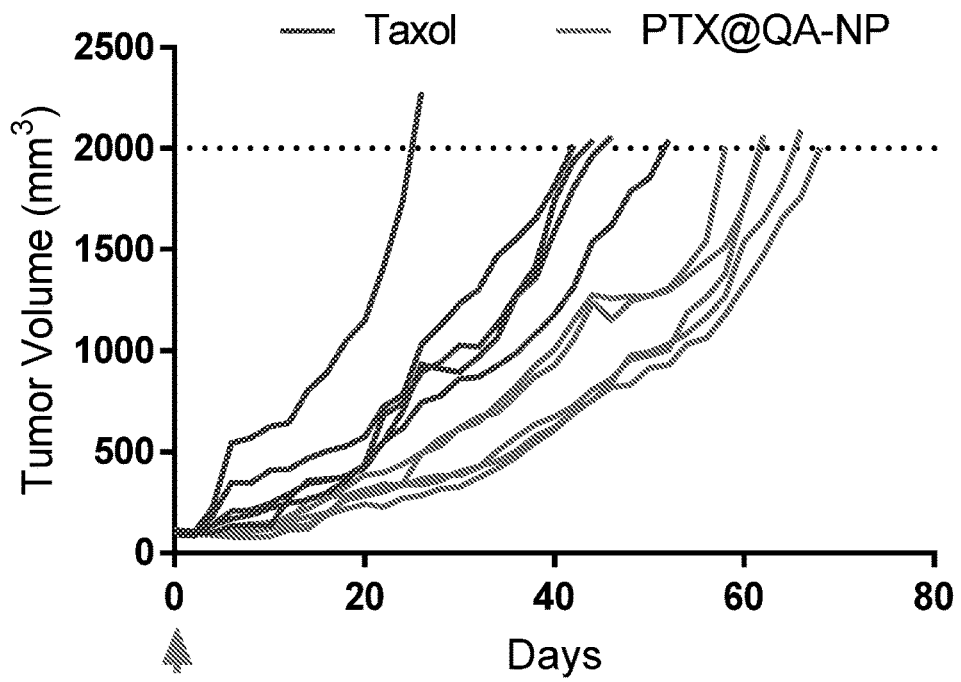
FIG. 8A shows treatments given as a single dose equivalent to PTX 20 mg/kg in female nude mice with MDA-MB-231 xenografts. Mice were sacrificed once the tumor volume (V) reached 2000 mm$^3$ or showed any signs of morbidity defined in the animal protocol. n=5 per group. Tumor specific growth rate is defined as $\Delta \log V/\Delta t$ (t: time in days). *: $p<0.05$ by unpaired t test.
Figure 8B:
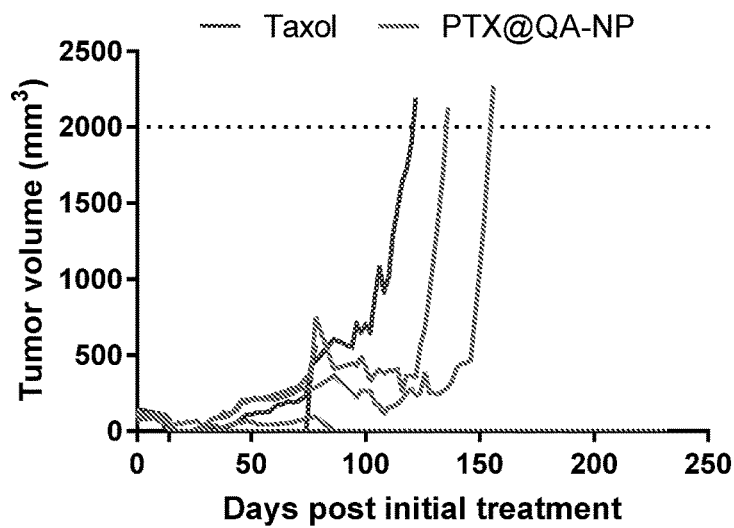
FIG. 8B shows treatments given as five doses of 20 mg PTX equivalent/kg/dose over 2 weeks in female nude mice with MDA-MB-231 xenografts. n=5 per group. *: $p<0.05$ by Gehan-Breslow-Wilcoxon test.

The anti-cancer efficacy of PTX@QA-NP was first tested with a single dose (20 mg/kg PTX equivalent) in a female nude mouse model of subcutaneous MDA-MB-231 tumor. Taxol, a commercial surfactant-solubilized PTX formulation, was used at the same dose as a reference. As shown in FIG. 8A, PTX@QA-NP attenuated the growth of MDA-MB-231 tumors more efficiently than Taxol. The median survival time of PTX@QA-NP was 62 days, significantly longer than that of Taxol (44 days, p<0.01, Log-rank test). The same regimen was administered to male C57BL/6 mice with syngeneic B16F10 tumors. Reflecting the known aggressive nature, the tumors grew much faster than MDA-MB-231, but PTX@QA-NP still induced superior tumor attenuation to Taxol at the same dose. Next, PTX@QA-NP was given every three days over 2 weeks (total five times: q3d×5) at 20 mg/kg/dose (FIG. 8B). PTX@QA-NP offered a significant survival benefit with 3 out of 5 animals showing complete remission by >200 days (as of the submission of this report), while only one surviving in the Taxol group during the same period. Two animals treated with Taxol reached the end point based on the tumor size, one with deteriorating health condition with an ulcerated tumor, and the other found dead with no apparent reason. These results collectively demonstrate that PTX@QA-NP brings greater anti-cancer efficacy than Taxol at the equivalent dose.

Anti-Cancer Efficacy: Comparison with PEG-NP

Figure 9A:
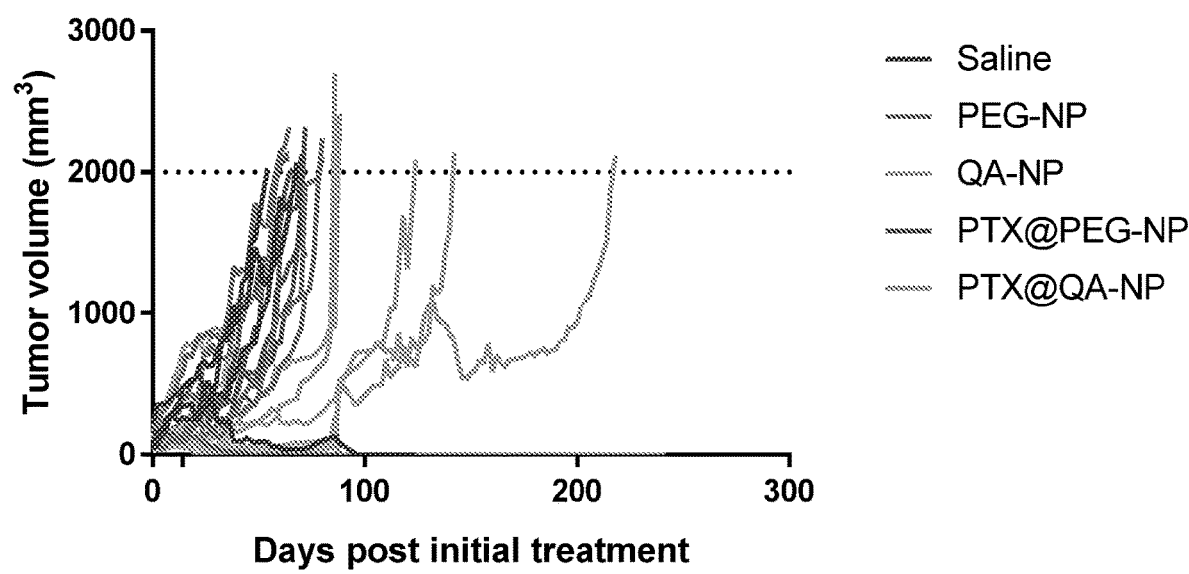
FIG. 9A shows anti-cancer efficacy of PTX@QA-NP in comparison with saline, blank PEG-NP, blank QA-NP, and PTX@PEG-NP. Treatments were given as 10 doses of 30 mg PTX equivalent/kg/dose over 2 weeks. n=5 per group.

We compared PTX@QA-NP with PTX@PEG-NP at the maximum tolerated dose determined. Healthy female nude mice survived 10 injections of PTX@QA-NP at 30 mg/kg/dose over 2 weeks without a significant weight loss. Therefore, female nude mice with subcutaneous MDA-MB-231 animals were treated with one of the following treatments 10 times over the period of 2 weeks: (i) saline; (ii) blank QA-NP; (iii) blank PEG-NP; (iv) PTX@PEG-NP at 30 mg/kg/dose; and (v) PTX@QA-NP at 30 mg/kg/dose. Only the PTX@QA-NP group showed a survival benefit compared to the saline group, with 40% complete remission as of >200 days (FIG. 9A). All other groups succumbed to death with a median survival time of 68 days (saline), 86 days (blank QA-NP), 80 days (blank PEG-NP), and 70 days (PTX@PEG-NP). It was surprising that the PTX@PEG-NP group was no better than the negative control groups with no surviving animals. We reasoned that PTX@PEG-NP may have induced the production of anti-PEG antibodies, which would accelerate the clearance of subsequently dosed PTX@PEG-NPs, as documented with PEGylated liposomes (Y Mima, et al., *Molecular Pharmaceutics* 2015, 12, 2429-2435; T Ishida, et al., *Journal of controlled release* 2003, 88, 35-42).

Figure 9B:
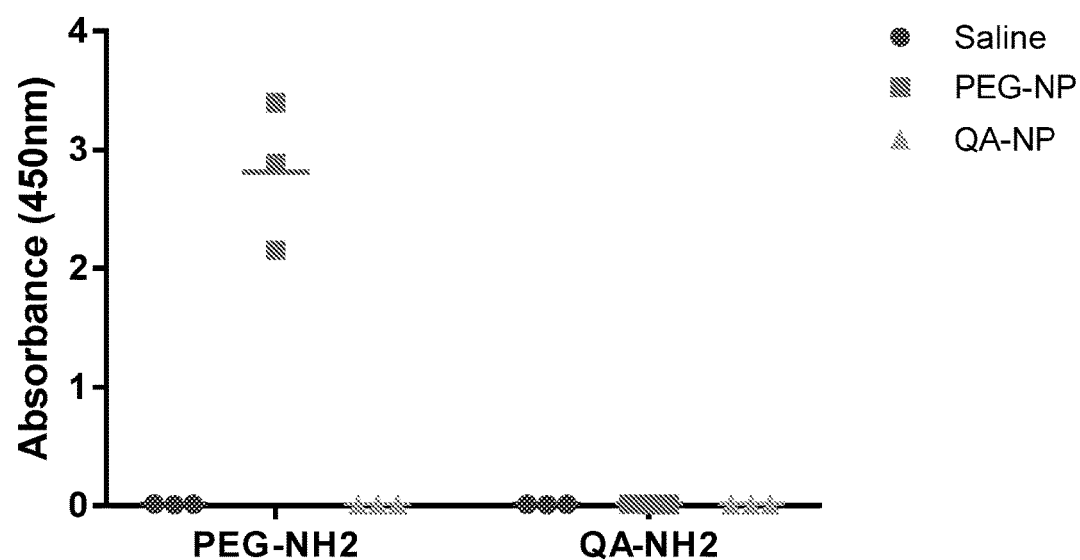
FIG. 9B shows detection of antibodies to each ligand (PEG, QA) 5 days after single injection of PEG-NP, QA-NP, or saline (as a negative control). n=3 per group. *: p<0.05 by Log-rank (Mantel-Cox) test.

To investigate this possibility, we treated healthy nude mice with saline, blank PEG-NP, or blank QA-NP, collected blood 5 days later, and added the serum to a plate coated with mPEG or QA to detect the presence of antibodies. Animals receiving PEG-NP produced antibodies that bound to PEG-decorated surface, while other treatments (saline, QA-NPs) did not (FIG. 9B). QA-NP injection did not induce the production of anti-QA antibodies. These results demonstrate that QA-NP delivered PTX to tumors more efficiently than PEG-NP by repeated administration.

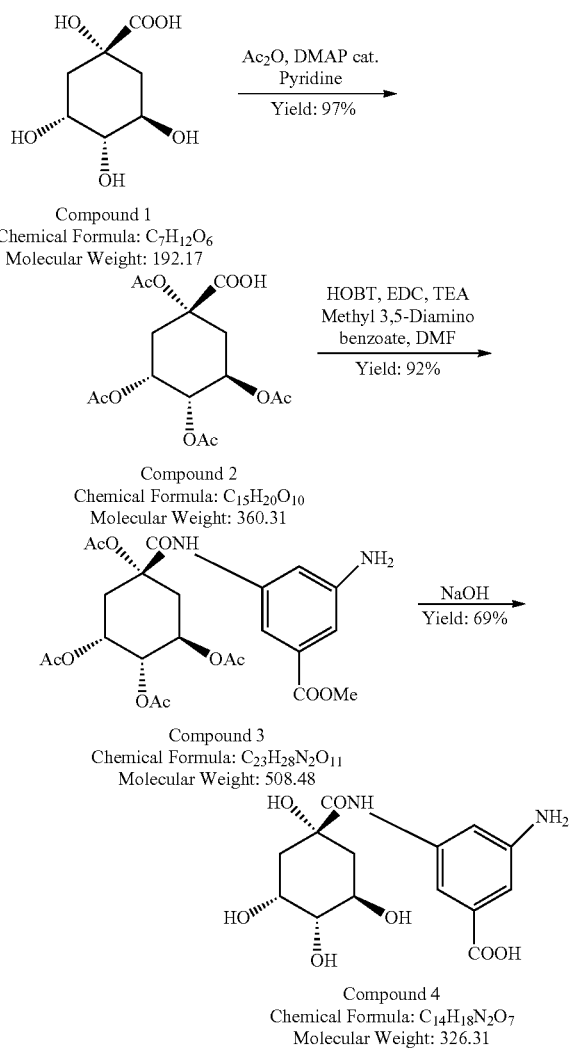

Scheme 1.
Synthesis of quinic acid (QA) derivative 4, a synthetic mimic of sLe$^x$ Compound 1
Chemical Formula: $C_7H_{12}O_6$
Molecular Weight: 192.17

Compound 2
Chemical Formula: $C_{15}H_{20}O_{10}$
Molecular Weight: 360.31

Compound 3
Chemical Formula: $C_{23}H_{28}N_2O_{11}$
Molecular Weight: 508.48

Compound 4
Chemical Formula: $C_{14}H_{18}N_2O_7$
Molecular Weight: 326.31

Materials and Methods

Materials.

PLGA (LA:GA=85:15, free acid, MW: 150 kDa), Fluorescein-conjugated PLGA (LA:GA=48:52, MW: 5 kDa), and PLGA-ethylene diamine (PLGA-NH$_2$, LA:GA=57:43, MW: 5 kDa) were purchased from Akina, Inc. (West Lafayette, Ind., USA). Indocyanine green-N-succinimidyl ester (ICG-NHS) was purchased from Intrace medical (Lausanne, Switzerland). Hoechst 33342 and recombinant human tumor necrosis factor-alpha (TNF-α) were purchased from Invitrogen (Eugene, Oreg., USA). Methoxy-polyethylene glycol-amine (mPEG-NH$_2$, MW: 5 kDa) was purchased from JenKem Technology USA (Allen, Tex., USA). Collagen I rat-tail was purchased BD Biosciences (San Jose, Calif., USA). Dopamine hydrochloride was purchased from Alfa Aesar (Ward Hill, Mass., USA). CellMask™ deep red membrane staining dye was purchased from ThermoFisher Scientific (Waltham, Mass., USA). E-selectin antibody (P2H3) FITC and E-selectin antibody (UZ5) FITZ were purchased from Santa Cruz (Dallas, Tex., USA). Transwell polycarbonate membrane cell culture inserts (6.5 mm) with 3.0 μm pore were purchased from Corning (Corning, N.Y., USA). All other materials were purchased from Sigma-Aldrich (St. Louis, Mo., USA).

Synthesis of QA-NH$_2$ (1S,3R,4S,5R)-1,3,4,5-tetraacetoxycyclohexane-1-carboxylic Acid (Compound 2)

Quinic acid (compound 1, 961 mg, 5 mmol) was dissolved in 12 mL of acetic anhydride-pyridine 1:2 mixture. The solution was mixed with 4-dimethylaminopyridine (20 mg, 0.16 mmol) and stirred for 12 h at 5° C. The reaction mixture was then added to ice water, acidified to pH 3 and extracted with dichloromethane (DCM). The extract was dried with sodium sulphate and concentrated to give a white solid (1.75 g, 97% Yield). ESI: (M+H)$^+$: 361.

(1R,2S,3R,5S)-5-((3-amino-5-(methoxycarbonyl)phenyl)carbamoyl)cyclohexane-1,2,3,5-tetrayl Tetraacetate (Compound 3)

Compound 2 (958 mg, 2.7 mmol) was dissolved in 15 mL of dimethylformamide. The solution was mixed with N-Hydroxybenzotrizole (432 mg, 3.2 mmol) and stirred for 5 min at 0° C. (1-ethyl-3-[3-dimethylaminopropyl] carbodiimide (612 mg, 3.2 mmol) and triethyl amine (0.5 mL, 4.3 mmol) were then added to the mixture ad stirred for 1 h at 0° C. Finally, a solution of methyl 3,5-diaminobenzoate (1.7 g, 7.7 mmol) in dimethylformamide (5 mL) was added to the mixture, which was warmed up to room temperature and stirred for 72 h. The reaction mixture was then added to ice water and extracted with DCM. The extract was dehydrated with sodium sulfate, filtered and further evaporated. The residue was purified by column chromatography on silica gel (hexane-ethyl acetate 3:7) to yield a brown solid compound (1.3 g, 92% Yield). ESI: (M+H)$^+$: 509.

3-amino-5-((1 S,3R,4S,5R)-1,3,4,5-tetrahydroxycyclohexane-1-carboxamido)benzoic Acid (Compound 4)

A solution of compound 3 (102 mg, 0.2 mmol) in tetrahydrofuran (5 mL) was stirred with lithium hydroxide monohydrate (63 mg, 1.5 mmol) for 48 h at room temperature. The reaction mixture was then acidified to pH 5 using Amberlite acidic resin, filtered, and purified by reverse column chromatography on $C_{18}$-reversed phase silica gel (water-acetonitrile 1:2) to yield a white solid compound (45 mg, 69% Yield). ESI: (M+H)$^+$: 327.

Synthesis of ICG-Conjugated PLGA

Two hundred milligrams of PLGA-ethylene diamine was dissolved in 2 mL DMSO at room temperature. 1.5 mg of ICG-NHS was dissolved in 1 mL DMSO at room temperature with rigorous vortex mixing. One milliliter of N,N-diisopropylethylamine (DIPEA) was added to PLGA solution, followed by dropwise addition of ICG-NHS solution. The mixture was constantly stirred for 2 h, put in a regenerated cellulose dialysis bag with a molecular weight cut off of 3,500 Da (SpectrumLabs, Rancho Dominguez, Calif., USA) and dialyzed against excess DMSO 3 times and DCM 3 times. The purified sample was collected via rotary evaporation and stored at −20° C.

Preparation of Core PLGA NPs

Core PLGA NPs were produced by the single emulsion solvent evaporation method. In brief, 100 mg of PLGA was dissolved in 4 mL of DCM. The polymer solution was added to 12 mL of a 4% polyvinyl alcohol (PVA) solution and emulsified using a Sonics Vibracell probe sonicator (Sonics, Newtown, Conn., USA) for 2 minutes. The emulsion was added to 40 mL of deionized water and stirred for 4 h to evaporate DCM. The NPs were then collected by centrifugation using an Optima MAX-XP ultracentrifuge (Beckman Coulter, Brea, Calif., USA) and washed with deionized (DI) water three times. For confocal microscopy and flow cytometry, NPs were prepared with fluorescein-conjugated PLGA. For optical in vivo imaging, NPs were prepared with ICG-conjugated PLGA.

Particle Surface Modification

The core NPs were coated with pD by 3 h incubation in 2 mL of dopamine hydrochloride solution in Tris buffer (10 mM, pH 8.5) at room temperature with rotation. The pD-coated PLGA NPs (NP-pD) were collected by ultracentrifugation and washed twice with DI water. For further surface functionalization, NP-pD were resuspended in Tris buffer containing QA-NH$_2$ or mPEG, maintaining the weight ratio of NP-pD to the ligands at 1:2. After 30 min incubation, the NPs were collected via ultracentrifugation and washed with DI water twice. The surface-functionalized NPs were designated as NP-pD-QA (or QANPs) and NP-pD-PEG, respectively.

Quantification of QA-NH$_2$ Ligand Density

A known amount of NP-pD was resuspended in Tris buffer (10 mM, pH 8.5) containing a known amount of QA-NH$_2$ (QA-NH$_2$ feed). After 30 min incubation, the NPs were collected via ultracentrifugation, and the supernatant was analyzed by HPLC to determine the amount of unconjugated free QA-NH$_2$. The surface-conjugated QA-NH$_2$ was calculated by subtracting free QA-NH$_2$ from QA-NH$_2$ feed. The QA-NH$_2$ ligand density was calculated by dividing the number of surface-conjugated QA-NH$_2$ with the total surface area of NP-pD.

Particle Characterization

NPs were dispersed in phosphate buffer (1 mM, pH 7.4), and their sizes and zeta potentials were measured by a Malvern Zetasizer Nano ZS90 (Worcestershire, UK). NP morphology was observed by Tecnai™ transmission electron microscopy (FEI, Hillsboro, Oreg., USA) after negative staining with uranyl acetate. QA-NH$_2$ surface decoration was confirmed by electrospray ionization mass spectrometry (ESI-MS) analysis of QANPs. PEG-NH$_2$ surface decoration was confirmed by.

Serum Stability of QANPs

For evaluating size stability, 5 mg of QANPs were suspended in 5 mL of 50% FBS and incubated for 2 h at room temperature. Particle size distribution was measured by a Malvern Zetasizer Nano Z590. For evaluating fluorescence stability, ICG-labeled QANPs were suspended in 50% FBS. NP pellet and supernatant were separated by ultracentrifugation at pre-specified time points and imaged with IVIS Lumina to detect fluorescence intensity.

Cell Culture

Human umbilical vein endothelial cells (HUVECs, ATCC, Manassas, Va., USA) at passage 4 were grown in EGM-2 complete medium. Culture plates were pre-coated with 5 μg/cm$^2$ of rat tail collagen type I. Human breast adenocarcinoma cells (MDA-MB-231, ATCC; MCF-7, ATCC) were cultured in Dulbecco's modified eagle's medium (DMEM) supplemented with 10% fetal bovine serum (FBS). Human colon adenocarcinoma cells (LS174T, ATCC) were cultured in Eagle's minimum essential complete medium (EMEM) supplemented with 10% FBS. Human ovarian cancer cells (A2780, ATCC) were cultured in Gibco™ RPMI 1640 medium (RPMI) supplemented with 10% FBS. Human ovarian cancer cells (NCI/ADR-RES)

were cultured in DMEM supplemented with 10% FBS. All media were supplemented with 100 units/mL penicillin and 100 μg/mL streptomycin. All cells were subcultured at a ratio of 1:7.5 when they became 70-80% confluent.

Confocal Microscopy and Flow Cytometry

HUVECs were seeded in a 35 mm dish with a glass window (MatTek Corporation, Ashland, Mass., USA) coated with rat tail collagen type I and grown in EGM-2 Bullet Kit complete medium. When HUVECs were approximately 80% confluent, cells were incubated with EGM-2 containing 10 ng/mL of TNF-α for 4 hours. The medium was replaced with EGM-2 containing 0.2 mg/mL of fluorescently-labeled NP suspension and incubated for 2 hours at 37° C. The suspension was replaced with fresh EGM-2 medium containing 0.5 μM CellMask™ deep red membrane staining dye. After 10 minutes, cells were gently washed with PBS twice. Hoechst nuclear stain (10 μL at the concentration of 0.2 mg/mL) was added 10 minutes prior to the imaging. Confocal microscopic imaging was performed using a Nikon A1R confocal microscope equipped with a Spectra Physics 163C argon ion laser and a Coherent CUBE diode laser. The NPs, cell nuclei, and cell membrane were excited using 346, 633, and 649 nm laser, respectively.

For flow cytometry, HUVECs were treated with NPs in the same way as above and gently washed with PBS twice to remove free or loosely bound NPs. The cells were then trypsinized, collected by centrifugation at 930×g for 5 minutes, resuspended in 0.2 mL of PBS at 0° C., and analyzed with an Accuri C6 flow cytometer (BD Biosciences, San Jose, Calif., USA) equipped with an FL-1 detector ($\lambda_{ex}/\lambda_{em}$=488/525 nm). For competition assay, known concentrations of free QA-NH$_2$ or E-selectin antibody were pre-incubated with HUVECs for 30 minutes, prior to the NP treatment and flow cytometry.

Transendothelial Migration Assay

HUVECs were seeded in a Corning Transwell insert coated with rat tail collagen type I and grown in EGM-2 Bullet Kit complete medium. The transendothelial electrical resistance (TEER) across the Transwell insert was monitored daily by EVOM2™ epithelial voltohmmeter (World Precision Instruments, Sarasota, Fla., USA). When the TEER value across the insert reached a plateau, cells were treated with 10 ng/mL of TNF-α for 4 hours, followed by incubation with 0.1 mg/mL of fluorescently-labeled QANPs for 8 hours. The fluorescence intensity of total NPs prior to incubation and those of NPs in the lower and upper Transwell compartments after incubation period were measured by FluoroMax 3 spectrofluorometer (Horiba Scientific, Edison, N.J., USA).

Endothelial Upregulation of E-Selectin by Tumor-Conditioned Media

HUVECs were seeded in a 6-well plate coated with rat tail collagen type I at a density of 10,000 cells/cm$^2$. When HUVECs became approximately 70-80% confluent, cells were exposed to the culture media conditioned with MCF-7, MDA-MB-231, LS174T, A2780, and NCI-ADR cells for 4 h. HUVECs were trypsinized and collected via centrifugation. The cell pellets were resuspended in PBS and stained with 20 μL (equivalent to 1× manufacture suggested dose) of FITC labeled anti-E-selectin antibody. The extent of E-selectin upregulation, if any, was quantified by flow cytometry.

In Vivo Whole Body Imaging

All animal procedures were approved by the Purdue Animal Care and Use Committee, in compliance with the NIH guidelines for the care and use of laboratory animals. Female athymic nude mice (Foxn1$^{nu}$) at the age of 6-7 weeks were purchased from Envigo (Indianapolis, Ind., USA) and acclimatized for 1 week prior to the procedure. Each mouse received 5×10$^6$ MDA-MB-231 cells in the flank of hind leg by subcutaneous injection. When the averaged tumor volume reached 200 mm$^3$, each mouse received 6 mg of ICG labeled QANPs or NP-pD-PEG in PBS via tail vein injection. The animals were imaged with IVIS Lumina system (Caliper Life Sciences, Hopkinton, Mass., USA) to detect near infrared fluorescence signal over 48 hours. After 48 hours, mice were sacrificed, and tumors and major organs were retrieved and imaged with IVIS Lumina system. To quantify ICG content in each organ, tumor and major organs were homogenized in DMSO with a Tissue Master homogenizer (Omni International, Kennesaw, Ga., USA). The organ homogenates were centrifuged, and 0.1 mL supernatant was sampled from each homogenate and analyzed with the IVIS Lumina system.

Encapsulation of a Drug for Cancer Treatment in NPs

Both hydrophobic and hydrophilic cancer therapeutics can be readily encapsulated in NPs by following the art known to a person skilled in this field. In particular, using NPs made of polyesters and polyphenols to encapsulate a cancer treatment is provided below as examples. Examples of polyphenol compounds include tannic acid, pyrogallol, epicatechin gallate, epigallocatechin gallate, and the likes.

(i) Hydrophobic drugs are encapsulated in polyester NPs by the emulsion method.

Hydrophobic drug and polyester are dissolved in dichloromethane or ethyl acetate and emulsified in water solution containing an emulsifier. The solvent is evaporated by rotary evaporation with constant stirring. The solidified NPs are washed with water and lyophilized until use.

(ii) Hydrophilic drugs are encapsulated in polyester NPs by the emulsion method.

Hydrophilic drugs are dissolved in water and emulsified in an organic solution containing polyester. Thus formed primary emulsion is emulsified in water solution containing an emulsifier. The solvent is evaporated by rotary evaporation with constant stirring. The solidified NPs are washed with water and lyophilized until use.

(iii) Hydrophobic drugs are encapsulated in polyphenol nanocapsules.

Hydrophobic drug is dissolved in ethanol or other appropriate solvent and mixed with a concentrated ethanolic solution of tannic acid. To this mixture, a volume of water containing iron chloride is added to form drug-rich nano-cores coated with polymerized tannic acid assemblies at the interface. The particles are washed by centrifugation and resuspension in water several times to remove excess tannic acid, iron chloride and un-entrapped drug.

(iv) Hydrophilic drugs are encapsulated in polyphenol nanocapsules.

Hydrophilic drugs are dissolved in water in high concentration and dispersed in glycerol along with a surfactant. Immediately after the dispersion, tannic acid and iron chloride are added to stabilize the interface. The resulting NPs are washed with water to remove glycerol.

(v) Nanocrystalline hydrophobic drugs.

Hydrophobic drug and surfactant are dissolved in chloroform in a round-bottomed flask. The organic solvent is evaporated using a rotary evaporator to form a film, which is hydrated in water. The hydrated drug-surfactant mixture is sonicated to form nanocrystals, incubated with albumin and washed with water.

Statistical Analysis

All statistical analysis was performed with GraphPad Prism 7 (Location). All data were analyzed with one-way or two-way ANOVA test to determine the statistical significance of means among various groups, followed by Dunnett's or Bonferroni's multiple comparisons test. A p-value less than 0.05 was considered statistically significant.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A quinic acid-modified nanoparticle (QANP) selectively targeting E-selectin- or P-selectin-positive cells or tissues comprising:
   a. a nanoparticle (NP);
   b. a polyphenol compound comprising polymerized dopamine (pD), the pD coating the NP; and
   c. a quinic acid derivative having the following formula:

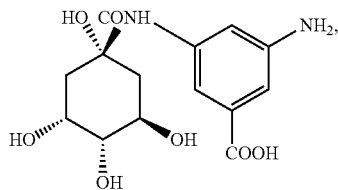

wherein said polyphenol compound is further modified by said quinic acid derivative by incubating the coated NP with the quinic acid derivative at a 1:2 weight ratio of coated NP to quinic acid derivative such that the quinic acid derivative conjugates to a surface of the coated NP in an orientation capable of selectin binding.

2. The QANP according to claim 1, wherein said NP is selected from the group consisting of poly(lactic-co-glycolic acid) (PLGA), polyethyleneglycol-PLGA conjugate, D-α-Tocopherol polyethylene glycol 1000 succinate (TPGS)-PLGA conjugate, polylactic acid (PLA), mesoporous silica, liposomes, and polyphenol aggregates.

3. The QANP according to claim 1, wherein said NP comprises one or more encapsulated therapeutic drugs.

4. The QANP according to claim 3, wherein said therapeutic drug is selected from the group consisting of paclitaxel, sorafenib, itraconazole, docetaxel, doxorubicin, bortezomib, carfilzomib, camptothecin, cisplatin, oxaliplatin, cytarabine, vincristine, irinotecan, amphotericin B, gemcitabine, polymyxin B, dexamethasone, and vitamin D.

5. The QANP according to claim 1, wherein the QANP has a quinic acid derivative (QA) density on the surface of the coated NP from 25 QA/nm$^2$ to 100 QA/nm$^2$.

6. The QANP according to claim 1, wherein said P-selectin or E-selectin-positive cells or tissues are cancerous cells or tissues, or endothelial cells surrounding cancerous cells or tissues.

7. A pharmaceutical composition comprising a QANP according to claim 1, further comprising one or more diluents, excipients or carriers.

8. The pharmaceutical composition according to claim 7, wherein said pharmaceutical composition is for treating a patient with cancer.

9. A process for manufacturing a quinic acid-modified nanoparticle (QANP) selectively targeting E-selectin- or P-selectin-positive cells or tissues comprising the steps of:
   a. preparing a nanoparticle (NP);
   b. coating said NP with a polyphenol compound comprising polymerized dopamine (pD); and
   c. modifying polyphenol coated NP with a quinic acid derivative to afford said QANP by suspending the coated NP in a first buffer containing the quinic acid derivative at a 1:2 weight ratio of coated NP to quinic acid derivative;

wherein the quinic acid derivative has the structure:

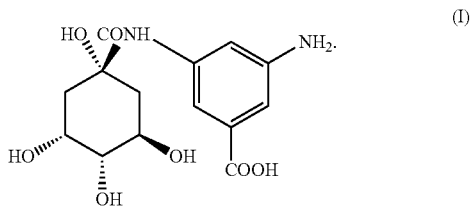

10. The process according to claim 9, wherein said NP comprises one or more therapeutic drugs.

11. The process according to claim 9, wherein suspending the coated NP in a first buffer containing the quinic acid derivative further comprises incubating the suspension for at or near 30 minutes.

12. The process according to claim 9, wherein coating said NP with a polyphenol compound further comprises suspending the NP in a dopamine hydrochloride solution in a second buffer, the second buffer comprising a 10 mM Tris buffer at pH 8.5.

13. The process according to claim 9, wherein said NP is made of PLGA, polyethyleneglycol-PLGA conjugate, D-α-Tocopherol polyethylene glycol 1000 succinate (TPGS)-PLGA conjugate, polylactic acid (PLA), mesoporous silica, liposomes, and polyphenol aggregates.

14. A pharmaceutical product manufactured according to the process of claim 9, together with one or more diluents, excipients or carriers.

15. The pharmaceutical composition of claim 14, wherein said NP comprises one or more therapeutic drugs.

16. The process according to claim 9, wherein said P-selectin or E-selectin-positive cells or tissues are cancerous cells or tissues, or endothelial cells surrounding cancerous cells or tissues.

17. A method for treating a patient of cancer comprising the step of administering to a patient in need of relief from said cancer a therapeutically effective amount of a pharmaceutical composition according to claim 7.

18. The pharmaceutical composition of claim 7, wherein the NP of the QANP is encapsulated and selected from the group consisting of poly(lactic-co-glycolic acid) (PLGA), polyethyleneglycol-PLGA conjugate, D-α-Tocopherol polyethylene glycol 1000 succinate (TPGS)-PLGA conjugate, polylactic acid (PLA), mesoporous silica, liposomes, and polyphenol aggregates.

19. The process according to claim 9, wherein the step of coating said NP is performed independent of, and prior to, the step of modifying polyphenol coated NP with a quinic acid derivative.

* * * * *